United States Patent [19]
Mooreville et al.

[11] Patent Number: 5,968,067
[45] Date of Patent: Oct. 19, 1999

[54] SURGICAL PENILE DILATOR INSTRUMENT AND METHOD FOR ITS USE

[76] Inventors: Michael Mooreville, 287 Sycamore Ave., Merion Station; Sorin Adrian, 311 Fawn Hill Ln., Penn Valley, both of Pa. 19072

[21] Appl. No.: 09/123,277

[22] Filed: Jul. 28, 1998

Related U.S. Application Data

[60] Provisional application No. 60/088,421, Jun. 8, 1998.

[51] Int. Cl.$^6$ .................................................. A61M 29/00
[52] U.S. Cl. .............................. 606/191; 606/167; 600/40
[58] Field of Search ...................................... 606/191, 167, 606/170, 185, 186; 600/39, 40

[56] References Cited

U.S. PATENT DOCUMENTS

| | | | |
|---|---|---|---|
| 4,411,260 | 10/1983 | Koss | 600/40 |
| 5,057,082 | 10/1991 | Burchette, Jr. | 606/167 |
| 5,217,481 | 6/1993 | Barbara . | |
| 5,823,970 | 10/1998 | Terwilliger | 606/167 |

*Primary Examiner*—Michael Buiz
*Assistant Examiner*—Kevin Truong
*Attorney, Agent, or Firm*—William H. Meise

[57] ABSTRACT

A tool, for forming a cavity in a corpus cavernosa of a penis, includes a distal end (14), a longitudinally-extending cutting surface (16), and a main body portion (18). The cutting portion may be cylindrical or tapered, and may contain more than one longitudinally disposed cutting surface (24). The tool may be made from stainless steel, or may include plastic portions. A method using the invention includes the steps of making an incision in the side of the penis adjacent the corpus cavernosa, and inserting the distal end of the tool into the spongy tissue, to define a cavity. If fibrous or resistant tissue is encountered, the cutting portion is brought adjacent the region, and the tool either moved axially to cut the tissue, or rotated about its longitudinal axis (8) to cut or shave the tissue. Multiple tools of a kit of tools may be sequentially inserted to expand the cavity to the desired dimension. When the cavity is completed, the object, which may be an expansible or inflatable chamber, is inserted into the cavity.

28 Claims, 10 Drawing Sheets

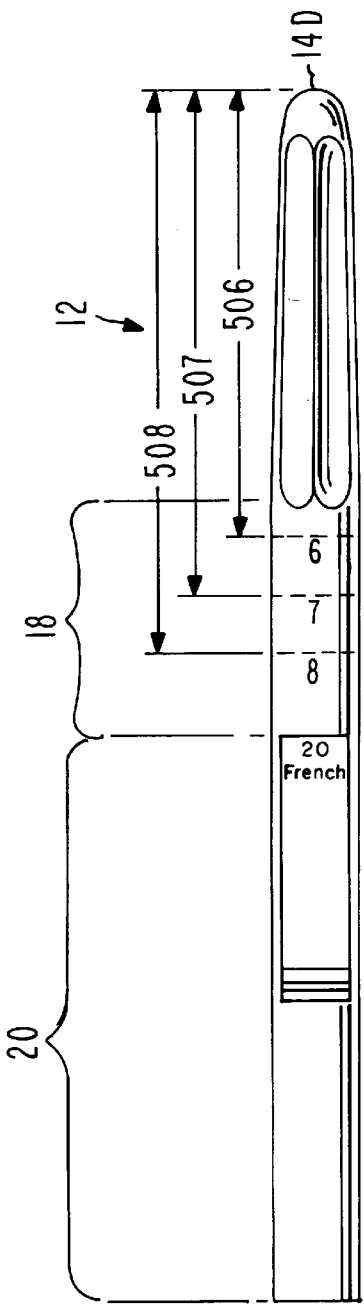

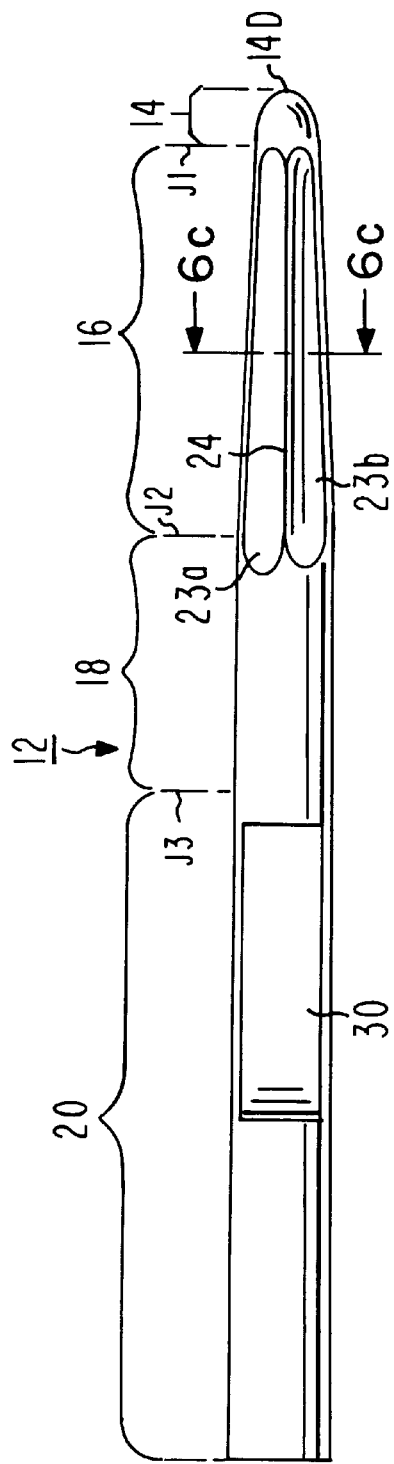

SURGICAL PENILE DILATOR INSTRUMENT AND METHOD FOR ITS USE

This application claims the benefit of the filing date of Provisional application Ser. No. 60/088,421, filed Jun. 8, 1998, now pending.

FIELD OF THE INVENTION

This invention relates to a tool for making a cavity for insertion of an object, such as an inflatable chamber, into the corpus cavernosa of the penis, and more particularly to a dilatation tool having a cutting surface.

BACKGROUND OF THE INVENTION

Penile prostheses are well known in the art for aiding in obtaining or maintaining an erection. An example of such a prosthesis is that described in allowed patent application Ser. No. 08/832,700, filed Apr. 12, 1997 in the names of the inventors herein, and entitled PENILE PROSTHESIS WITH PUMP ROTOR DIRECTLY ACTUATED BY ROTATING MAGNETIC FIELD. In the abovementioned patent application, and in other penile prostheses, two inflatable chambers are inserted into the penis, one on each side, in the part of the penis known as the corpus cavernosa. The corpus cavernosa lie on each side of the penis, and are formed from a spongy tissue, which normally become engorged with blood to cause an erection. When disfunction prevents normal erection, an prosthesis, including inflatable balloon or chamber inserted into each corpus cavernosa, can be implanted. When the chambers or balloons of the prosthesis are inflated, the same erection effect occurs as that attributable to engorgement with blood.

In the past, the chambers of a prosthesis were inserted into the corpus cavernosa by making an incision into the side of the penis adjacent the corpus cavernosa, and generally in the vicinity of the junction of the penis with the body. The incision provided access to the corpus cavernosa. Scissors were then used to cut into that portion of the corpus cavernosa extending proximally toward the body, and also into that portion extending distally toward the distal end of the penis. In other words, realizing that the penis includes portions which lie within the body, the access was obtained at about a mid-way point, and a cavity was made, as by use of scissors, scalpel, and dilator. This technique is not applicable in situations in which the spongy tissue within the corpora cavernosa is fibrotic such that adequate space for the prosthesis cannot be created.

U.S. Pat. No. 5,217,481, issued Jun. 8, 1993 in the name of Barbara, describes a surgical instrument which is used for dilatation and enlargement of a cavity in a corpus cavernosa. It includes a monolithic stainless steel tool with a rasp-like distal portion and a handle portion. Traction is applied to the tool, and the rasp-like or sawtooth projections cut as the tool is withdrawn. Various tool sizes are provided to allow the formation of different cavity sizes. The Barbara instrument is only an abrasive device, and the amount of tissue removal cannot be readily controlled. The shape and size of the device are such that it does not allow for easy penetration of hard, fibrotic tissue.

Improved surgical tools and methods for their use are desired.

SUMMARY OF THE INVENTION

A surgical tool, according to an aspect of the invention, for forming a cavity in the corpus of a penis, defines an axis of elongation, and includes an elongated body defining a distal portion, a cutting portion more proximal than the distal portion, a main portion more proximal than the cutting portion, and a handle portion more proximal than the main portion. The main portion of the body of the tool is circular in a cross-section taken orthogonal to said axis of elongation, and defines a first radius about the axis of elongation. The cutting portion including at least one cutting surface extending by about the first radius from the axis of elongation, and at least one other surface extending by the first radius from the axis of elongation. The distal portion of the body of the tool includes a generally circular cross-section, and has a radius, taken orthogonal to the axis of elongation which is tapered from a value equal to the radius of the cutting portion at the juncture of the cutting portion with the distal portion to a lesser radius at more distal locations.

In a particular embodiment of the apparatus according to the invention, the cutting portion has a constant radius of the cutting surface and of the other surface from the axis of elongation, whereby the cutting surface and the other surface lie on the surface of a cylinder. The most preferred embodiments of a tool according to this aspect of the invention have the cutting surface on a radius which is no larger than the radius of the other surface at the same longitudinal position. In a particular version of this particular embodiment, the tool has a dimension of the main portion which lies between 12 French and 40 French. A preferred embodiment of a tool according to this aspect of the invention is made from a biologically inert material, such as surgical-quality stainless steel. In one embodiment, a portion of the cutting portion is made from metal, and the remainder of the body is made from a plastic material. The handle portion may include at least one generally circular region having the first radius about the axis of elongation, and the handle portion may include a flat region, which preferably lies parallel with the axis of elongation. In a particularly advantageous version of this embodiment, a plane including the axis of elongation and passing orthogonally through the flat region includes an edge of at least one of the cutting surfaces. This orientation of the flat allows the user to determine the location of the cutting surface notwithstanding that the cutting surface is hidden during use.

In another advantageous embodiment of the tool according to an aspect of the invention, the cutting portion is tapered, and the at least one cutting surface extends by about the first radius from the axis of elongation at the juncture of the cutting portion with the main portion, and by a second radius, smaller than, or less than, the first radius, from the axis of elongation at the juncture of the cutting portion with the distal portion, and wherein the at least one other surface is likewise tapered, and extends by the first radius from the axis of elongation at the juncture of the cutting portion with the main portion, and by the second radius from the axis of elongation at the juncture of the cutting portion with the distal portion. The distal portion of the body of the tool has a generally circular cross-section, and is tapered from the second radius at locations near the cutting portion to a lesser radius at more distal locations. A tool according to an aspect of this embodiment has a dimension of the main portion lying between 12 French and 40 French. In a particularly advantageous embodiment of this aspect of the invention, the tool is made from a biologically inert material, such as surgical-quality stainless steel. In another advantageous embodiment, at least a portion of the cutting portion is made from metal, and the remainder of the body is made from a plastic material. In one embodiment, the handle portion includes at least one generally circular region, as viewed in a plane orthogonal to the axis of elongation, with the circular region having the first diameter about the axis of elongation. In another advantageous embodiment, a plane including the axis of elongation and passing orthogonally through the flat region includes an edge of at least one of the cutting surfaces.

A desirable manifestation of the invention has markings on the main portion of the body which indicate the distance from the distal end of the distal portion of the tool. These markings may include circumferentially-directed lines, together with marking indicating how far each line is from the distal end of the distal portion of the tool. Another desirable manifestation includes manufacturer's identification on the flat on the handle portion of the body of the tool. These markings may include an indication of the diameter of the tool, measured in millimeters or other standard indicators.

A method according to an aspect of the invention, for inserting an elongated object or chamber into a corpus of a penis, includes the step of obtaining access to the interior of a corpus of the penis of a patient; this may be done in any prior-art manner, such as making an incision into the side of the penis adjacent the corpus into which the object is to be inserted. The method includes the further step of obtaining or procuring a tool defining an axis of elongation. The tool so obtained or procured includes an elongated body defining a distal portion, a cutting portion more proximal than the distal portion, a main portion more proximal than the cutting portion, and a handle portion more proximal than the main portion. The main portion of the body of the tool is circular as seen in a cross-section perpendicular to the axis of elongation of the tool, and defines a first radius about the axis of elongation. The cutting portion of the tool includes at least one cutting surface extending by about the first radius from the axis of elongation at the juncture of the cutting portion with the main portion. In a preferred method according to the invention, the tool which is procured has a cutting surface which is straight, and which lies in a plane which includes the axis of elongation of the tool. The cutting portion of the tool procured according to this step of the method further includes at least one other surface extending by the first radius from the axis of elongation. The distal portion of the body of the tool includes a generally circular cross-section, and is tapered from the radius of the cutting portion at the juncture of the cutting portion with the distal portion to a lesser radius at more distal locations.

After the abovedescribed tool is procured, the distal portion of the tool is inserted into the corpus to the desired depth, approximately parallel with the axis of elongation of the penis. The tool may be held by its handle portion while inserting the distal end. If a fibrous region is encountered during the inserting step, The depth of penetration of the tool into the corpus is adjusted so that the cutting portion of the tool is adjacent to the fibrous region. The tool is then rotated about its longitudinal axis, either in a manner which sweeps the cutting surface across an arc in the vicinity of the fibrous region, or with complete rotations, to thereby tend to remove at least a portion of the fibrous region. Once the cavity in the corpus is of the proper dimension to accommodate the object or chamber, the tool is removed. The object or chamber is then inserted into the cavity.

The step of obtaining or procuring a tool may include the step of obtaining a tool having the first radius approximately equal to a corresponding radius of the object or chamber, or it may include the step of obtaining a tool in which the first radius makes a cavity which is smaller than the size of the chamber or object to be inserted, followed by a repetition of the entire set of actions with other tools of different first radii, until a cavity of suitable size is achieved. The step of obtaining a tool may include the step of obtaining a tool in which the cutting surface lies in or on the surface of a conceptual cylinder having a diameter equal to the first radius and coaxial with the axis of elongation. As an alternative, the step of obtaining a tool may include the step of obtaining a tool in which the cutting surface lies in or on the surface of a conceptual section, segment or frustum of a cone, which section, segment or frustum has a radius at its larger end which is equal to the first radius, and an axis which is coaxial with the axis of elongation.

According to another aspect of the invention, a kit of tools for aiding insertion of an object or chamber into the corpus of a penis includes a plurality of tools. Each of the tools defines an axis of elongation. Each of the tools further includes an elongated body defining a distal portion, a cutting portion more proximal than the distal portion, a main portion more proximal than the cutting portion, and a handle portion more proximal than the main portion. The main portion of the body of each of the tool is circular, as seen in a cross-section perpendicular to the axis of elongation, and defines a first radius about the axis of elongation. The cutting portion has at least one cutting surface extending by about the first radius from the axis of elongation at the juncture of the cutting portion with the main portion, and at least one other surface which, at any cross-section perpendicular to the axis of elongation, has a radius substantially equal to the radius of the cutting surface at the cross-section. The distal portion of the body of each of the tools has a generally circular cross-section, and is tapered from the radius of the cutting surface at locations near the cutting portion to a lesser radius at more distal locations. Each of the tools of the plurality of tools in one of the kits has a value of the first radius which differs from the value of the first radius of others of the tools in the kit, so that each kit contains no tools which are of identical size. A particularly advantageous kit of tools according to this aspect of the invention includes tools, the first radii of which include values in the range of about 3 to 7 millimeters. A kit having such values might have first radii of approximately 2, 3, 4, 5, 6, and 7 millimeters. The kit may include some tools which have tapered cutting portions and other tools which are nontapered or cylindrical.

In one avatar of the invention, the cutting surface of the tool is not tapered, but instead lies in (or on) the surface of a conceptual cylinder coaxial with the tool's axis of elongation. In another avatar, the cutting portion is tapered, and the cutting surface extends by a second radius, less than the first radius, at the juncture of the cutting portion with the distal portion.

BRIEF DESCRIPTION OF THE DRAWING

FIGS. 5a and 5b are plan and side elevation views, respectively, of a tool according to an aspect of the invention, illustrating how markings are placed on the tool;

FIGS. 6a, 6b, 6c, and 6d illustrate another embodiment, manifestation, or avatar of a tool according to an aspect of the invention, in which the cutting portion is tapered;

DESCRIPTION OF THE INVENTION

Figure 1A:
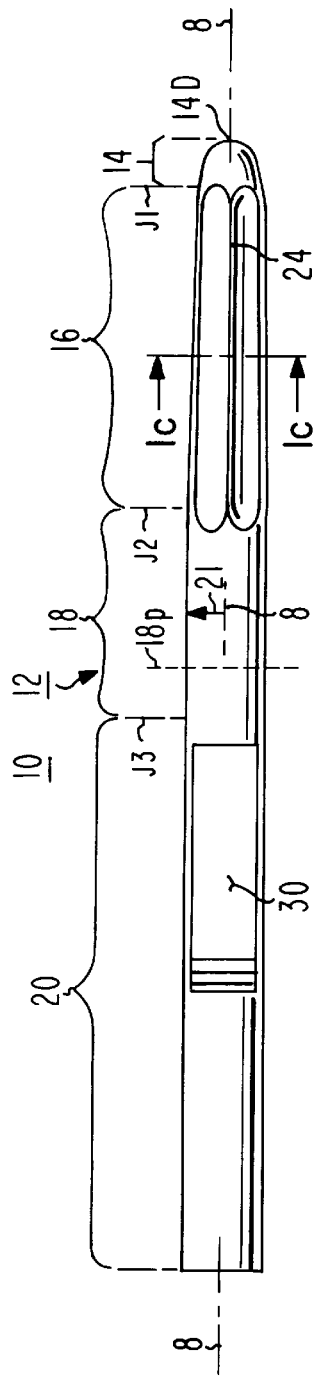
FIGS. 1a, 1b, 1c, and 1d are plan, side elevation, first and second cross-sectional views, respectively, of a tool according to an aspect of the invention.

FIGS. 1a, 1b, 1c, and 1d are plan, side elevation, first and second cross-sectional views, respectively, of a tool according to an aspect of the invention. In FIGS. 1a, 1b, 1c, and 1d, a tool 10 includes a body designated generally as 12. Body 12 is generally elongated along the direction of an axis of elongation or symmetry 8. Body 12 is divided into four portions, namely a distal portion 14, a cutting portion 16, a main body portion 18, and a handle portion 20. Distal portion 14 is tapered, and connects with cutting portion 16 at a junction designated J1; cutting portion 16 joins or connects with main portion 18 at a junction designated J2, and main portion 18 joins handle portion 20 at a third junction J3. As illustrated, these junctions are not specific planes, but rather represent transitions over a range of locations. Main portion 18 of body 12 has a circular cross-section as seen in a plane, such as plane 18p, orthogonal to axis 8, and the radius of the circular cross-section is designated 22. Cutting portion 16 of body 12 would have the same circular cross-section, but as a result of cavities or depressions 23a and 23b cut, formed or defined in the sides thereof, has a protruding cutting surface or edge designated 24. The term "protruding" in this case is with respect to the bottoms of the depressions 23a and 23b. However, the cutting surface or edge 24 is at the same radius 22 from axis 8 as the outer surface of the main body 18, and the cutting surface or edge 24 is also at the same radius 22 from the axis 8 as a second or noncutting surface 25. Thus, the cutting surface or edge 24 does not protrude beyond a circle centered at axis 8 and having radius 22.

Those skilled in the art will recognize that the cutting surface or edge 24 can be precisely at the radius 22, or slightly above or below the radius 24, with the difference being in the amount of material which is shaved from the surrounding surface when the cutting surface is swept through an angle. Thus, the cutting surface 24 can be at "about" the radius 22, which term is intended to connote a small deviation, no greater than about 5%. Those skilled in the art will also recognize that cutting surface 24, if thin and knife-edge-like, will tend to cut longitudinally during insertion of the dilatation tool 10 into the corpus cavernosa. This longitudinal cut will have a depth which depends upon the location of cutting surface 24 relative to the noncutting second surface 25; if cutting surface 24 is depressed below the adjacent surfaces of the tool, the cut will be shallow, and if it protrudes beyond the adjacent surfaces, the cut will be deeper.

As illustrated in FIGS. 1a, 1b, 1c, and 1d, the distal portion 14 of the body 12 of tool 10 has a circular cross-section as seen in a plane orthogonal to axis 8, and the radius of the circular cross-section in the distal region 14 is designated $R_{14}$. The dimension represented by radius $R_{14}$ depends upon where the cross-section is taken, since the distal portion is somewhat tapered, being smaller at more distal locations. At the juncture $J_1$ of the distal portion 14 with cutting portion 16, there is no step in the diameter, so the dimension $R_{14}$ must be equal to the radius of curvature 22 at the juncture J1. The taper of the distal portion 14 is intended to allow penetration of the corpus cavernosa, even if it should be fibrous.

Figure 1B:
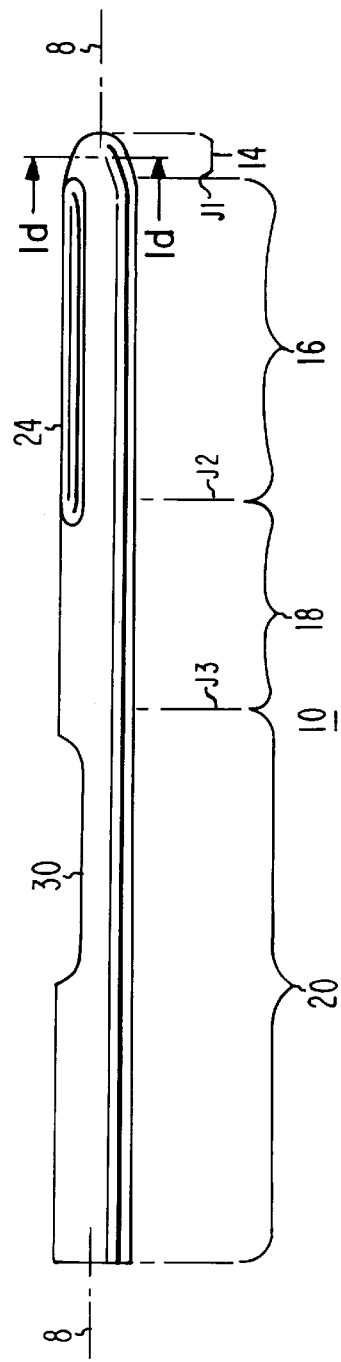
Figure 1C:
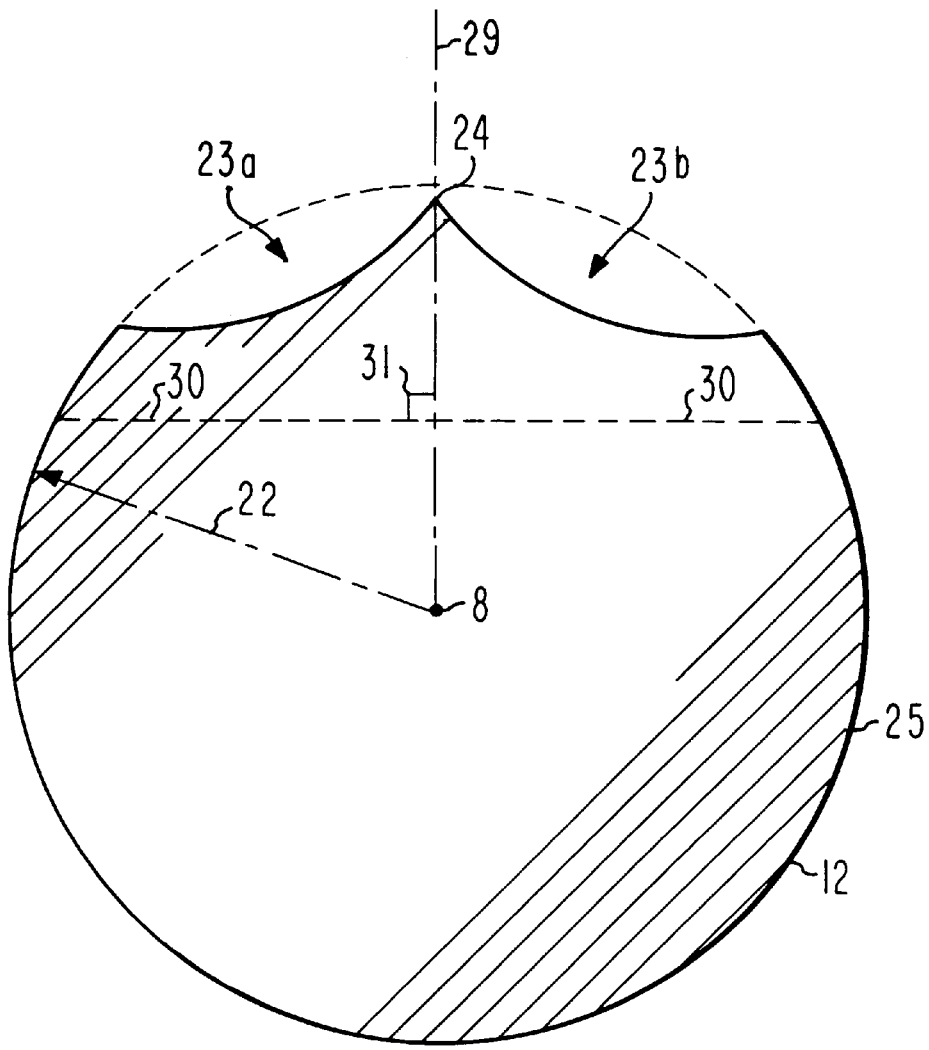
Figure 1D:
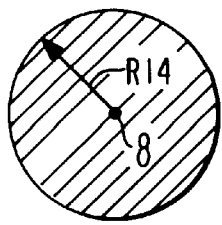

The handle portion 20 of the body 12 of the tool 10 of FIGS. 1a and 1b includes a flat portion or region 30. Flat portion or region 30 is indexed to the position of the cutting surface 24 as illustrated in FIG. 1c. More particularly, as illustrated in FIG. 1c, flat 30 is oriented relative to the cutting surface 24 in such a manner that a plane 29, passing orthogonally through flat 30 as illustrated by symbol 31, and including the axis 8, also passes through, and includes, the cutting surface 24. The reference to planes brings up the issue that a plane has no dimension, and a cutting surface has a finite dimension; in this case, the relationship is conceptual, and assumes that the cutting surface is thin. If the cutting surface is thick, the relationship is that plane 29 passes symmetrically between the two sides of the thick cutting surface 24. Thus, cutting surface 24 lies longitudinally, parallel with a plane 29 which includes the longitudinal axis 8, and does little or no cutting during insertion or withdrawal of the tool, depending upon the protrusion of the cutting surface, as mentioned above. Instead, the tool must be rotated about its axis in order to perform or shaving of tissue.

Figure 2:
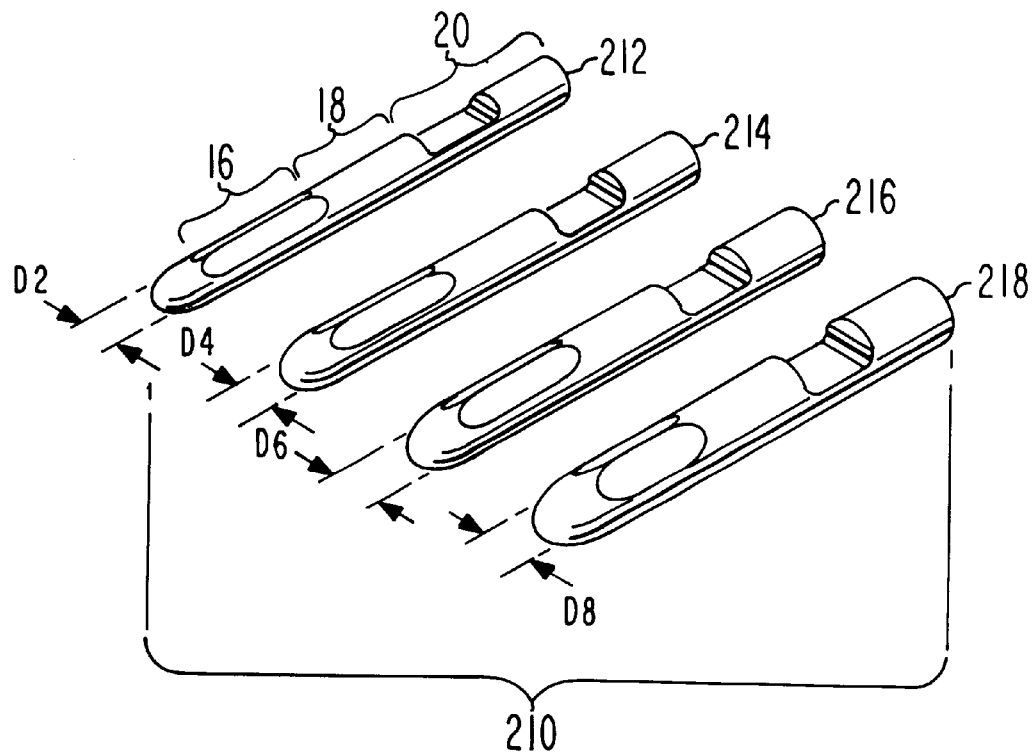
FIG. 2 illustrates a kit including a plurality of tools, each of which is similar, except for dimensions, to that illustrated in FIGS. 1a, 1b, 1c, and 1d.

The radius 22 of main portion 18 of body 12 of tool 10 of FIGS. 1a, 1b, 1c, and 1d is selected to expand the diameter of the cavity cut into the corpus cavernosa of a penis in the desired amount. According to an aspect of the invention, a kit of tools is provided, in which each tool has a different diameter. More specifically, FIG. 2 illustrates a kit 210 including a plurality, four in number, of tools 212, 214, 216, and 218, each of which is similar to that illustrated in FIGS. 1a, 1b, 1c, and 1d, but which have different diameters, designated as D2, D4, D6, and D8, respectively, which may correspond, for example, with a range of from 12 to 40 French, or they may have diameters which are measured in millimeters, with tool 212 having a diameter D2 of about 3 mm, tool 214 having a diameter D4 of about 4 mm, tool 216 having a diameter D6 of about 5 mm, and tool 218 having a diameter D8 of about 6 mm.

Figure 3:
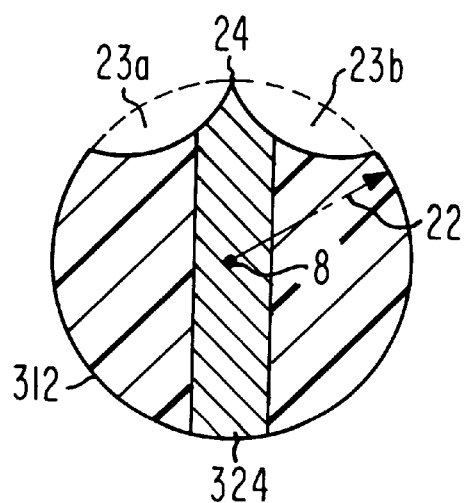
FIG. 3 is a cross-section of the cutting portion of a tool similar to that of FIGS. 1a, 1b, 1c, and 1d, in which the cutting surface is made from a different material than the body of the tool.

In one embodiment of the invention, the tools of FIGS. 1a, 1b, 1c, and 1d, and FIG. 2, are made from surgical-grade stainless steel. In another embodiment, in which the tools may be inexpensive enough to be disposable, the tool is made with a body of plastic, and with a cutting surface which is metallic. FIG. 3 is a cross-section of the cutting portion of a tool according to this aspect of the invention. In FIG. 3, the cross-section is similar to that of FIG. 1c, but the cutting surface 24 is part of a metal insert designated 324, and the remainder of the body, designated 312, is made from plastic material.

Figure 4:
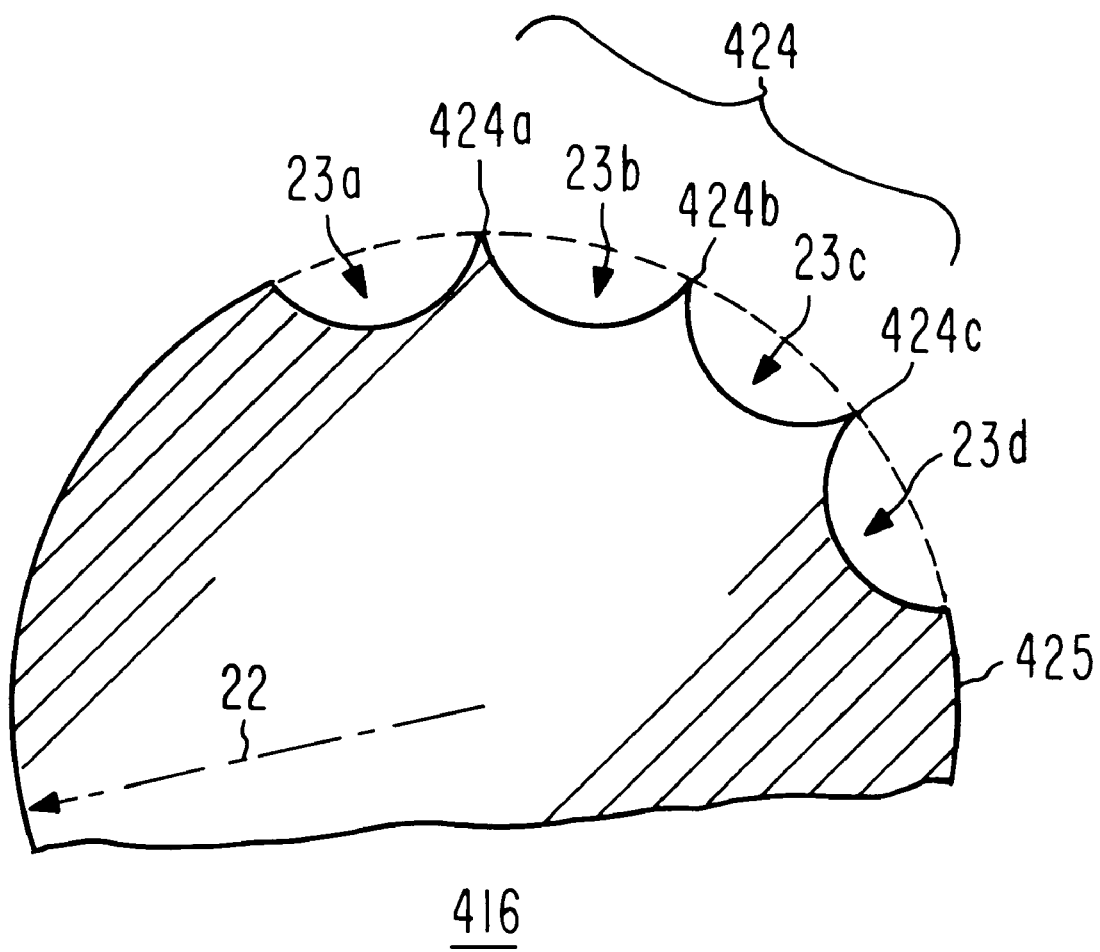
FIG. 4 is a cross-section of the cutting portion of a tool according to another aspect of the invention, in which the tool has a plurality of cutting surfaces.

FIG. 4 is a cross-section of the cutting portion 416 of a tool according to another aspect of the invention. In FIG. 4, there is a set 424 of three cutting surfaces 424a, 424b, and 424c, separated by depressions or cavities 23a, 23b, 23c, and 23d. In addition to the three cutting surfaces, the cutting portion 416 of FIG. 4 also has one additional or other surface 426, which is a non-cutting surface at the same radius 22 from center axis 8 as the cutting surfaces of set 424. As described in conjunction with FIG. 3, the structure of FIG. 4 may be made of a combination of different materials.

FIGS. 5a and 5b are similar to FIGS. 1a and 1b, but illustrate how markings may be placed on the body 12 of a tool according to an aspect of the invention. In FIGS. 5a and 5b, the main portion 18 of body 12 has markings in the form of partially-circumferential lines and associated numerals, which as illustrated are the numerals "6", "7", and "8". These numerals are each associated by proximity with one of the circumferential markings, and identify the distance between the circumferential marking and the distal tip 14D of the tool. Thus, the circumferential marking associated with the numeral "6", is six centimeters from distal tip 14D, as indicated by dimension 506 of FIG. 5a. Similarly, the circumferential markings associated with the numerals "7" and "8" are at distances indicated by dimensions 507 and 508, respectively, from distal end or tip 14D. The flat 30 defined in the handle portion 20 of the tool of FIGS. 5a and 5b bears markings indicating the nominal dilatation dimension, in the illustration "20 French," and may also bear manufacturer's identification markings.

Figure 6C:
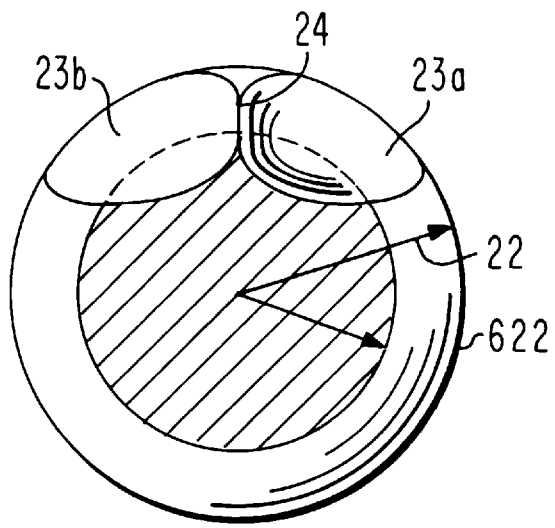
Figure 6D:
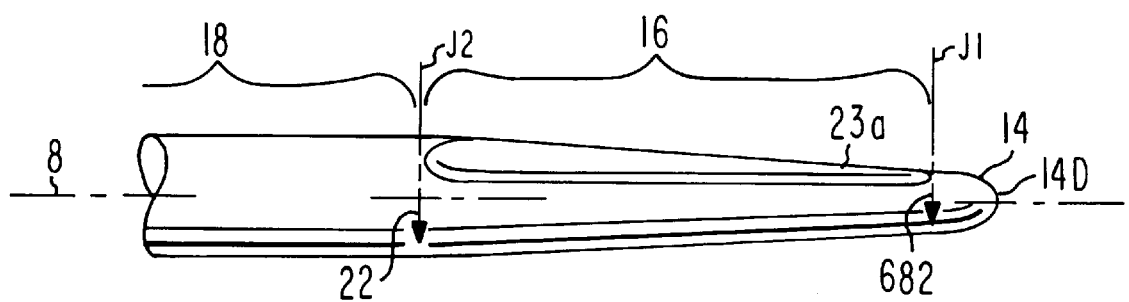

FIGS. 6a, 6b, 6c, and 6d illustrate another embodiment, manifestation, or avatar of a tool according to an aspect of the invention, in which the cutting portion is tapered. More particularly, the arrangement of FIGS. 6a, 6b, 6c, and 6d illustrates a tool in which the radius of the body 12 is 22 in the main portion 18, and begins to taper from a radius of 22 at the juncture J2 between the main portion 18 and the proximal end of the cutting portion 16. The taper continues to about the juncture J1 between the distal portion 14 and the distal end of the cutting portion 16. As illustrated in FIG. 6c, the radius at juncture J2 is 22, and the smaller radius at the plane 6c—6c is designated 622. Thus, the radius of the tapered cutting portion 16 of FIGS. 6a, 6b, 6c, and 6d at the location at which it joins each of the adjacent portions, namely the main portion 18 and the distal portion 14, is the same as the radius of that adjacent portion at the juncture. More specifically, the radius of the body at juncture J1 is designated 682, and this radius 682 is the same for the distal portion 14 and cutting portion 16 at locations immediately adjacent to juncture J1. Similarly, the radius of the body at juncture J2 is designated 22, and is the same for both the cutting portion 16 and the main portion 18 at locations immediately adjacent juncture J2. As illustrated in FIGS. 6a, 6b, 6c, and 6d, the taper is monotonic, but could be other than monotonic.

Figure 7A:
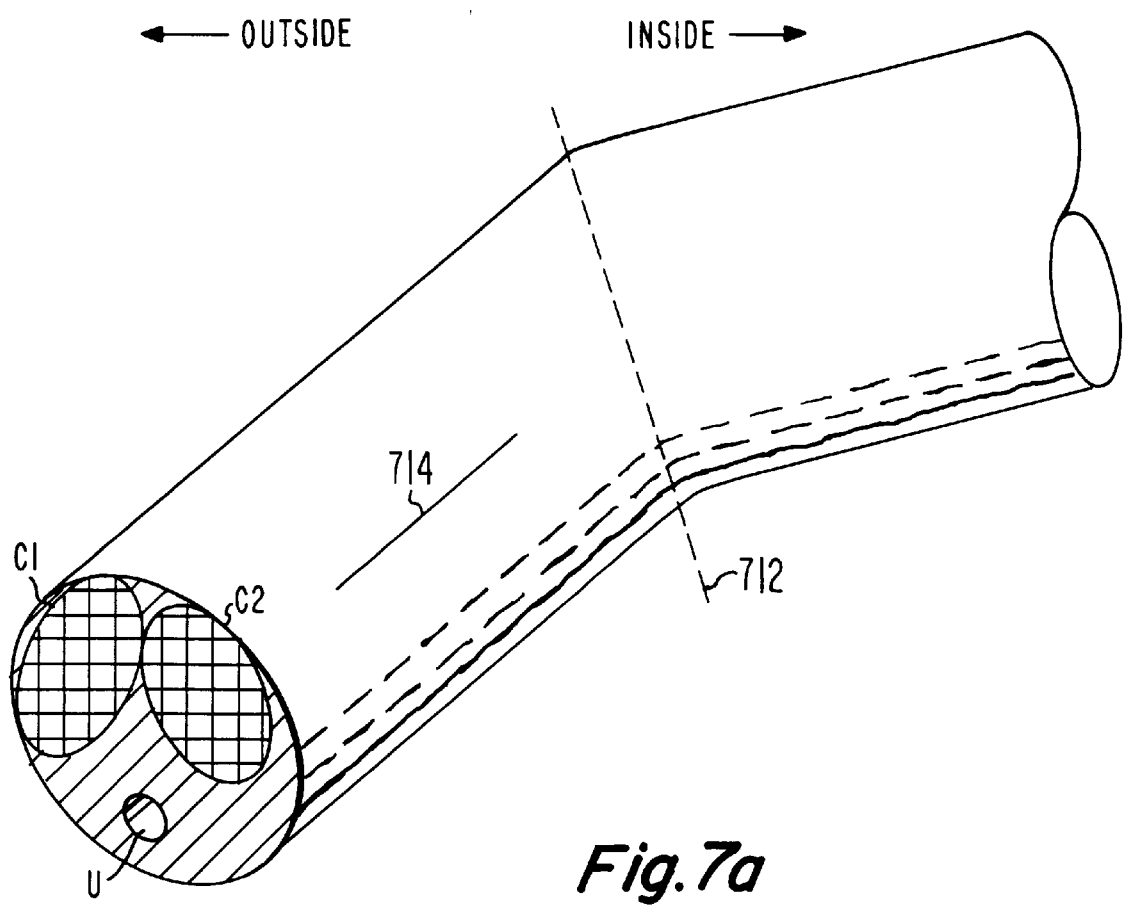
FIGS. 7a, 7b, 7c, and 7d are illustrations which aid in understanding a method according to the invention, using the tools described in relation to preceding FIGURES.

FIG. 7a is a simplified diagram of a penis, illustrating the locations of the corpus cavernosa, and the location at which an incision is made to begin the method according to an aspect of the invention. In FIG. 7a, the penis is designated generally as 710, and the plane of the bulk of the supporting body is designated 712. Regions inside and outside the body are designated by corresponding words and arrows. The corpus cavernosa are illustrated as C1 and C2, and the urethra is illustrated as U. An incision 714 is made at a location proximal from the distal end (not explicitly illustrated) of the penis 710, and near the body surface 712, over one of the two corpora, namely C2. The incision is spread, and a tool, such as any one of the tools according to the invention which has been described above, is inserted, distal end 14 first, into corpus cavernosa C2, and is pushed longitudinally into the penis, to begin to make an elongated cavity which will accept an object to be inserted. A typical object is an inflatable chamber portion of a penile prosthesis. Ordinarily, the dilatation tool diameter with which the procedure begins will be the smallest of the tools. However, the smallest one of the tools may not make a cavity as large as is required.

Figure 7B:
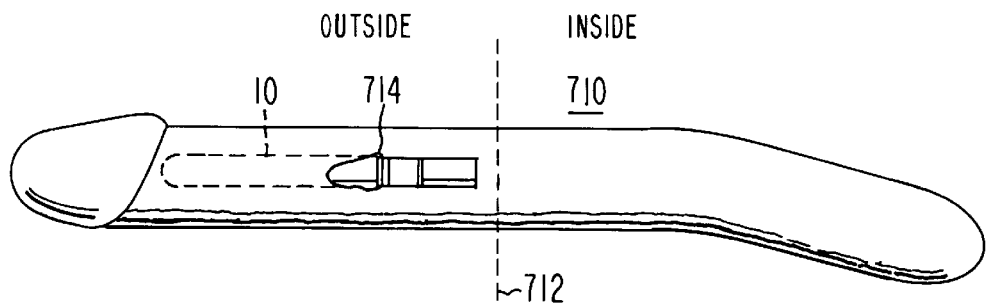
Figure 7C:
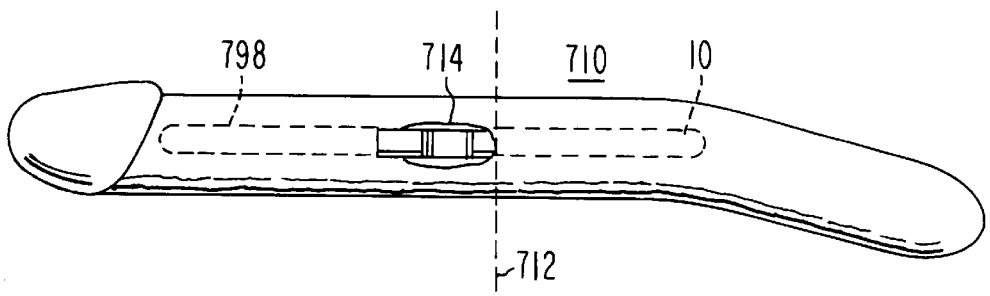
Figure 7D:
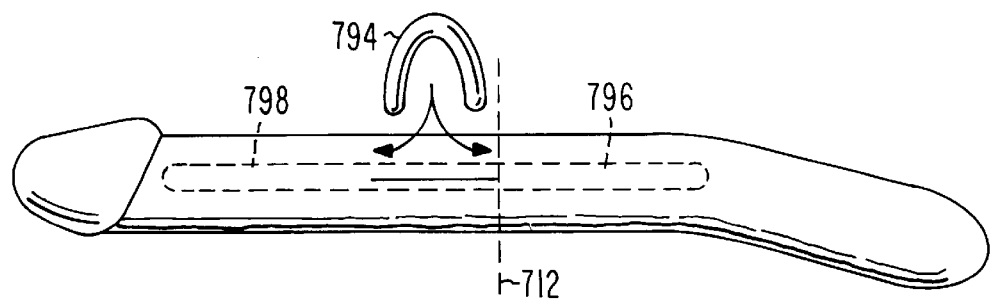

As the insertion of the first tool proceeds, the spongy tissue of the corpus cavernosa ordinarily gives only slight resistance, so the insertion toward the distal end of the penis may be readily accomplished, as illustrated by the step of FIG. 7b. The tool is then removed from the distal portion of the penis, leaving a cavity illustrated as 798 in FIG. 7a. The tool 10 is then reversed, and the distal end 14D (see FIGS. 1a or 6a) of the tool is inserted into that portion of the corpus cavernosa C2 which is more proximal than the incision 714, as illustrated in FIG. 7c. Assuming that no fibrous or resistant tissue is encountered, the proximal end of the chamber is formed within the proximal portion of corpus cavernosa C2; the proximal chamber portion is designated 796 in FIG. 7d. FIG. 7d illustrates the cavities 796 and 798 remaining in the corpus cavernosa C2 after the tool is removed. If the cavities 796 and 798 are large enough to accommodate the object to be inserted, the insertion can be done in conjunction with, or after the step of FIG. 7d. If the cavities 796 and 798 are not large enough, the cavities must be enlarged by repetition of the steps described in conjunction with FIGS. 7b, and 7c. Eventually the cavities which remain in corpus cavernosa C2 will be large enough, and the object may be inserted. It must be realized that an inflatable chamber, such as might be inserted in conjunction with a penile prosthesis, and illustrated in FIG. 7d as 794, is relatively flexible, and can readily be inserted, in the direction suggested by arrows 792, through incision 714, and fitted into the proximal and distal cavities 798 and 796, respectively. Following the insertion step illustrated in conjunction with FIG. 7d, the incision 714 may be closed. The procedure is repeated on the other side of the penis in relation to corpus cavernosa C1. So long as the tool is not rotated about its axis during the insertion, only a single "scribe" cut at the location of the cutting surface 24 (of FIG. 1a, for example) will occur during insertion. Unlike the use of the Barbara tool, removal of the tool according to the invention does not, itself, cut or remove tissue from the cavity.

Figure 8:
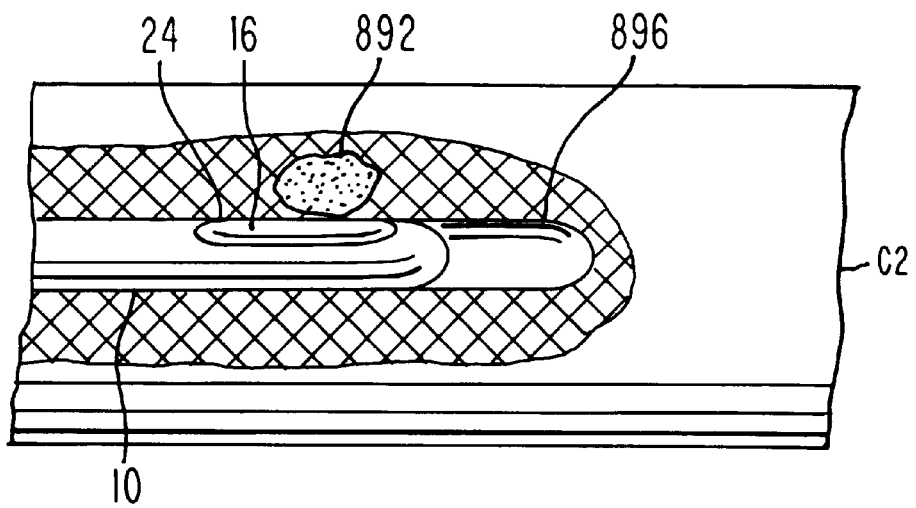
FIG. 8 is a representation of a portion of a corpus cavernosa of a penis during treatment according to an aspect of the invention.

As described above in conjunction with FIGS. 7a, 7b, 7c, and 7d, the tool was easily inserted into the corpus cavernosa, because no fibrous or resistant tissue was encountered. Fibrous tissue, if present, is seldom uniformly distributed. Its presence in substantial quantities may make insertion of the dilatation tool difficult. The uneven distribution of fibrous tissue tends to cause the tool, during insertion, to wander or deviate from the desired path, which is generally longitudinal. When the tool is deviated from a longitudinal path, the resultant cavity tends to be formed in the softer or spongier portion of the tissue adjacent to the more resistant fibrous tissue. The presence of fibrous tissue distributed through a portion of the corpus cavernosa, then, tends to cause the cavity to deviate from a "straight" path. This deviation may make subsequent insertion of the object into the cavity more difficult, and may also undesirably lead to uneven or asymmetrical results, which may lead to dissatisfaction on the part of the patient. According to an aspect of the invention, when fibrous tissue is felt, the tool 10 (for example) according to the invention is adjusted in position, as illustrated in FIG. 8, so that the cutting portion 16 is adjacent to the fibrous tissue 892. The cavity portion illustrated as 896 is the cavity which was developed in corpus cavernosa C2 at the time the fibrous tissue was felt, and is not filled with tool, because the tool was partially withdrawn, to bring cutting region 16 adjacent to the fibrous matter. In addition to having the cutting portion at the proper location, the cutting surface 24 must be moved to an angular position relative to the longitudinal axis of the tool at which the cutting surface 24 can engage the fibrous tissue 892. This is readily accomplished by noting the position of the flat, and adjusting the position of the flat to coincide with the perceived position of the fibrous tissue 892. The tool is then rotated about its longitudinal axis 8, to thereby sweep the cutting surface 24 in an arc across the region having the fibrous matter. The number of sweeps can be selected to remove the appropriate amount of fibrous matter. When the cavity goes approximately "straight" through the fibrous matter, and the sweeping procedure is stopped. The tool can then be further advanced to increase the depth of the cavity, or if sufficiently deep, the tool may be removed, and the next step performed.

Figure 9:
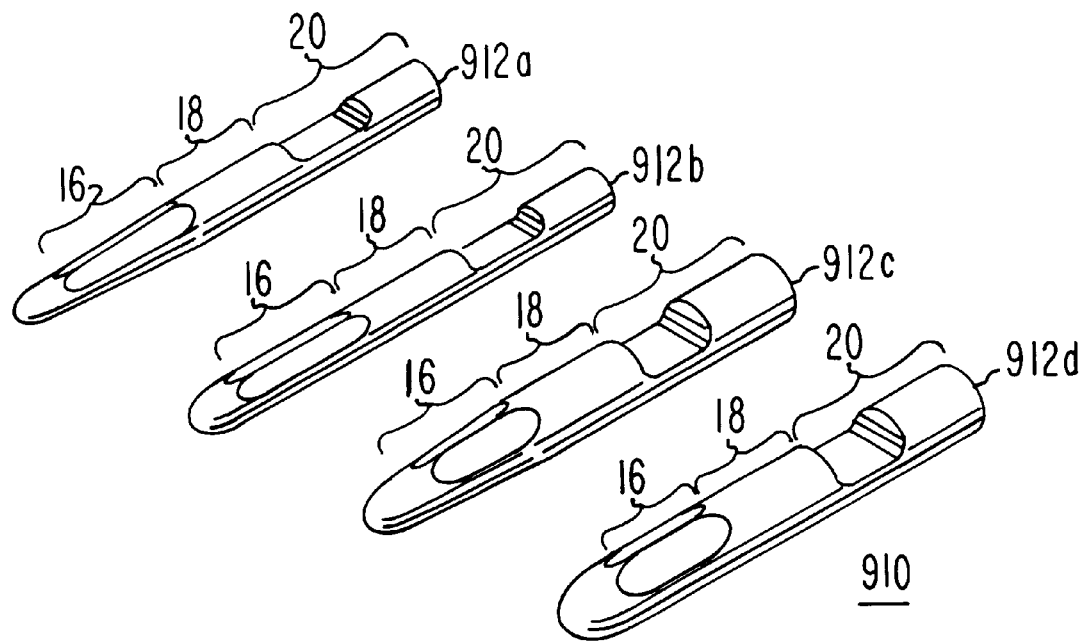
FIG. 9 illustrates a kit of parts in which some of the dilators are tapered, and others are cylindrical.

FIG. 9 illustrates a kit or set of tools 910 in which the set includes both tapered and cylindrical instruments. In FIG. 9, the instruments 912a and 912b have the same body diameter, but instrument 912a is tapered, and instrument 912b is cylindrical. Similarly, instruments 914a and 914b have the same body diameter, which is larger than the body diameter of instruments 912a and 912b, but instrument 914a is tapered, and instrument 914b is cylindrical.

Other embodiments of the invention will be apparent to those skilled in the art. For example, as mentioned in the Barbara patent, the shape of the handle is irrelevant, and it may be made in any convenient shape and size, which may even vary among the different tools of a kit. While the method has been described in detail only for one of the tools according to the invention, any of the tools may be used with the method. While a particular range of tool sizes has been described, the tool sizes may be appropriate to the needs of the application.

Thus, a surgical tool (10), according to an aspect of the invention, for forming a cavity in the corpus of a penis, defines an axis of elongation (8), and includes an elongated body (12) defining a distal portion (14), a cutting portion (16) more proximal than the distal portion (14), a main portion (18) more proximal than the cutting portion (16), and a handle portion (20) more proximal than the main portion (18). The main portion (18) of the body (12) of the tool (10) is circular in a cross-section taken orthogonal to said axis of elongation (8), and defines a first radius (22) about the axis of elongation (8). The cutting portion (16) includes at least one cutting surface (24) extending by about the first radius (22) from the axis of elongation (8), and at least one other surface (25, 425) extending by the first radius (22) from the axis of elongation (8). In a most preferred embodiment of the invention, the cutting surface (24) extends by no more than the first radius (22) from the axis of elongation, and the other surface (25, 425) lies at the first radius (22) at any selected longitudinal position along the cutting portion (16). The distal portion (14) of the body (12) of the tool (10) includes a generally circular cross-section, and has a radius ($R_{14}$), taken orthogonal to the axis of elongation (8) which is tapered from a value equal to the radius of the cutting portion (16) at the juncture of the cutting portion (16) with the distal portion to a lesser radius at more distal locations.

In a particular embodiment of the apparatus according to the invention, the cutting portion (16) has a constant radius of the cutting surface (24) and of the other surface (25, 425) from the axis of elongation (8), whereby the cutting surface (24) and the other surface (25, 425) lie on the surface of a cylinder. In a particular version of this particular embodiment, the tool (10) has a dimension of the main portion (18) which lies between 12 French and 40 French. A preferred embodiment of a tool (10) according to this aspect of the invention is made from a biologically inert material, such as surgical-quality stainless steel. In one embodiment, a portion of the cutting portion (16) is made from metal, and the remainder of the body (12) is made from a plastic material. The handle portion (20) may include at least one generally circular region having the first radius (22) about the axis of elongation (8), and the handle portion (20) may include a flat region (30), which preferably lies parallel with the axis of elongation (8). In a particularly advantageous version of this embodiment, a plane (29) including the axis of elongation (8) and passing orthogonally (31) through the flat region (30) includes an edge of at least one of the cutting surfaces (24). This orientation of the flat allows the user to determine the location of the cutting surface notwithstanding that the cutting surface is hidden during use.

In another advantageous embodiment of the tool according to an aspect of the invention, the cutting portion (16) is tapered, and the at least one cutting surface (24) extends by about the first radius (22) from the axis of elongation (8) at the juncture of the cutting portion (16) with the main portion (18), and by a second radius, smaller than, or less than, the first radius (22), from the axis of elongation (8) at the juncture of the cutting portion (16) with the distal portion (14), and wherein the at least one other surface is likewise tapered, and extends by the first radius (22) from the axis of elongation (8) at the juncture of the cutting portion (16) with the main portion (18), and by the second radius from the axis of elongation (8) at the juncture of the cutting portion (16) with the distal portion. The distal portion (14) of the body (12) of the tool (10) has a generally circular cross-section (FIG. 1c), and is tapered from the second radius at locations near the cutting portion (16) to a lesser radius at more distal locations. A tool (10) according to an aspect of this embodiment has a dimension of the main portion (18) lying between 12 French and 40 French. In a particularly advantageous embodiment of this aspect of the invention, the tool (10) is made from a biologically inert material, such as surgical-quality stainless steel. In another advantageous embodiment, at least a portion of the cutting portion (16) is made from metal, and the remainder of the body (12) is made from a plastic material. In one embodiment, the handle portion (20) includes at least one generally circular region, as viewed in a plane orthogonal to the axis of elongation, with the circular region having the first diameter (D) about the axis of elongation (8). In another advantageous embodiment, a plane (29) including the axis of elongation (8) and passing orthogonally (31) through the flat region (30) includes an edge (24) of at least one of the cutting surfaces (24).

A desirable manifestation of the invention has markings on the main portion (18) of the body (12) which indicate the distance from the distal end (14D) of the distal portion (14) of the tool (10). These markings may include circumferentially-directed lines, together with marking indicating how far each line is from the distal end (14D) of the distal portion (14) of the tool (10). Another desirable manifestation includes manufacturer's identification on the flat (30) on the handle portion (20) of the body (12) of the tool (10). These markings may include an indication of the diameter of the tool, measured in millimeters or other standard indicators.

A method according to an aspect of the invention, for inserting an elongated object or chamber into a corpus of a penis, includes the step of obtaining access to the interior of a corpus of the penis of a patient; this may be done in any prior-art manner, such as making an incision into the side of the penis adjacent the corpus into which the object is to be inserted. The method includes the further step of obtaining or procuring a tool (10) defining an axis of elongation (8). The tool so obtained or procured includes an elongated body (12) defining a distal portion (14), a cutting portion (16) more proximal than the distal portion (14), a main portion

(18) more proximal than the cutting portion (16), and a handle portion (20) more proximal than the main portion (18). The main portion (18) of the body (12) of the tool (10) is circular as seen in a cross-section perpendicular to the axis of elongation of the tool, and defines a first radius (22) about the axis of elongation (8). The cutting portion (16) of the tool (10) includes at least one cutting surface (24) extending by about the first radius (22) from the axis of elongation (8) at the juncture of the cutting portion (16) with the main portion (18). In a preferred method according to the invention, the tool which is procured has a cutting surface which is straight, and which lies in a plane which includes the axis of elongation of the tool. The cutting portion (16) of the tool procured according to this step of the method further includes at least one other surface (25, 425) extending by the first radius (22) from the axis of elongation (8). The distal portion (14) of the body (12) of the tool (10) includes a generally circular cross-section, and is tapered from the radius of the cutting portion (16) at the juncture of the cutting portion (16) with the distal portion to a lesser radius at more distal locations.

After the abovedescribed tool is procured, the distal portion (14) of the tool (10) is inserted into the corpus to the desired depth, approximately parallel with the axis of elongation (8) of the penis. The tool (10) may be held by its handle portion (20) while inserting the distal end. If a fibrous region is encountered during the inserting step, The depth of penetration of the tool (10) into the corpus is adjusted so that the cutting portion (16) of the tool (10) is adjacent to the fibrous region. The tool is then rotated about its longitudinal axis, either in a manner which sweeps the cutting surface across an arc in the vicinity of the fibrous region, or with complete rotations, to thereby tend to remove at least a portion of the fibrous region. The tool may also be pushed back and forth axially, with slight rotations between each insertion, to thereby make a series of longitudinal cuts in the corpus cavernosa. Once the cavity in the corpus is of the proper dimension to accommodate the object or chamber, the tool is removed. The object or chamber is then inserted into the cavity.

The step of obtaining or procuring a tool (10) may include the step of obtaining a tool (10) having the first radius (22) approximately equal to a corresponding radius of the object or chamber, or it may include the step of obtaining a tool in which the first radius makes a cavity which is smaller than the size of the chamber or object to be inserted, followed by a repetition of the entire set of actions with other tools of different first radii, until a cavity of suitable size is achieved. The step of obtaining a tool (10) may include the step of obtaining a tool (10) in which the cutting surface (24) lies in or on the surface of a conceptual cylinder having a diameter equal to the first radius (22) and coaxial with the axis of elongation (8). As an alternative, the step of obtaining a tool (10) may include the step of obtaining a tool (10) in which the cutting surface (24) lies in or on the surface of a conceptual section, segment or frustum of a cone, which section, segment or frustum has a radius at its larger end which is equal to the first radius (22), and an axis which is coaxial with the axis of elongation (8).

According to another aspect of the invention, a kit (210) of tools for aiding insertion of an object or chamber into the corpus of a penis includes a plurality of tools (10). Each of the tools (10) defines an axis of elongation (8). Each of the tools further includes an elongated body (12) defining a distal portion (14), a cutting portion (16) more proximal than the distal portion (14), a main portion (18) more proximal than the cutting portion (16), and a handle portion (20) more proximal than the main portion (18). The main portion (18) of the body (12) of each of the tools (10) is circular, as seen in a cross-section perpendicular to the axis of elongation, and defines a first radius (22) about the axis of elongation (8). The cutting portion (16) has at least one cutting surface (24) extending by about the first radius (22) from the axis of elongation (8) at the juncture of the cutting portion (16) with the main portion (18), and at least one other surface (25, 425) which, at any cross-section perpendicular to the axis of elongation (8), has a radius substantially equal to the radius of the cutting surface (24) at the cross-section. The distal portion (14) of the body (12) of each of the tools (10) has a generally circular cross-section, and is tapered from the radius of the cutting surface (24) at locations near the cutting portion (16) to a lesser radius at more distal locations. Each of the tools (10) of the plurality of tools (10) in one of the kit (210)s has a value of the first radius (22) which differs from the value of the first radius (22) of others of the tools (10) in the kit (210), so that each kit (210) contains no tools which are of identical size. A particularly advantageous kit (210) of tools according to this aspect of the invention includes tools, the first radii of which include values in the range of about 3 to 7 millimeters. A kit (210) having such values might have first radii of approximately 3, 4, 5, and 6 millimeters.

In one avatar of the invention, the cutting surface (24) of the tool (10) is not tapered, but instead lies in (or on) the surface of a conceptual cylinder coaxial with the tool's axis of elongation (8). In another avatar, the cutting portion (16) is tapered, and the cutting surface (24) extends by a second radius, less than the first radius (22), at the juncture of the cutting portion (16) with the distal portion (14). A kit according to one embodiment of the invention includes dilatation tools, some of which have tapered cutting portions, and other tools which are nontapered or cylindrical.

What is claimed is:

1. A surgical tool for forming a cavity in the corpus of a penis, said tool defining an axis of elongation, and comprising:

an elongated body defining a distal end, a cutting portion more proximal than said distal end, a main portion more proximal than said cutting portion, and a handle portion more proximal than said main portion;

said main portion of said body of said tool being circular, and defining a first radius about said axis of elongation;

said cutting portion including at least one cutting surface extending by about said first radius from said axis of elongation, and at least one other surface extending by said first radius from said axis of elongation; and said distal end of said body of said tool including a generally circular cross-section, and being tapered from the radius of said cutting portion at the juncture of said cutting portion with said distal end to a lesser radius at more distal locations.

2. A tool according to claim 1, wherein said cutting surface of said cutting portion does not protrude beyond said first radius.

3. A tool according to claim 1, wherein said cutting portion has a constant radius of said cutting surface and of said other surface from said axis of elongation, whereby said cutting surface and said other surface lie on the surface of a cylinder.

4. A tool according to claim 3, wherein said tool has a dimension of said main portion which lies between 12 French and 40 French.

5. A tool according to claim 3, wherein said tool is made from a biologically inert material.

6. A tool according to claim 5, wherein said tool is made from surgical-quality stainless steel.

7. A tool according to claim 5, wherein at least a portion of said cutting portion is made from metal, and the remainder of said body is made from a plastic material.

8. A tool according to claim 3, wherein said handle portion includes at least one generally circular region having said first radius about said axis of elongation.

9. A tool according to claim 8, wherein said handle portion includes a flat region.

10. A tool according to claim 9, wherein said flat region lies parallel with said axis of elongation.

11. A tool according to claim 9, wherein a plane including said axis of elongation and passing orthogonally through said flat region includes an edge of at least one of said cutting surfaces.

12. A surgical tool according to claim 1, wherein:
said cutting portion is tapered, and said at least one cutting surface extends by about said first radius from said axis of elongation at the juncture of said cutting portion with said main portion, and by a second radius, less than said first radius, from said axis of elongation at the juncture of said cutting portion with said distal end, and wherein at least one other tapered surface extends by said first radius from said axis of elongation at said juncture of said cutting portion with said main portion, and by said second radius from said axis of elongation at said juncture of said cutting portion with said distal end; and
said distal end of said body of said tool has a generally circular cross-section, and is tapered from said second radius at locations near said cutting portion to a lesser radius at more distal locations.

13. A tool according to claim 12, wherein said tool has a dimension of said main portion lying between 12 French and 40 French.

14. A tool according to claim 12, wherein said tool is made from a biologically inert material.

15. A tool according to claim 14, wherein said tool is made from surgical-quality stainless steel.

16. A tool according to claim 14, wherein at least a portion of said cutting portion is made from metal, and the remainder of said body is made from a plastic material.

17. A tool according to claim 14, wherein said handle portion includes at least one generally circular region having a first diameter about said axis of elongation.

18. A tool according to claim 12, wherein said handle portion includes a flat region which lies parallel with said axis of elonation, wherein a plane including said axis of elongation and passing orthogonally through said flat region includes an edge of at least one of said cutting surfaces.

19. A method for inserting a chamber into the corpus of a penis, said method comprising the steps of:
obtaining access to the interior of a corpus of the penis of a patient;
obtaining a tool defining an axis of elongation, and comprising:
an elongated body defining a distal end, a cutting portion more proximal than said distal end, a main portion more proximal than said cutting portion, and a handle portion more proximal than said main portion;
said main portion of said body of said tool being circular, and defining a first radius about said axis of elongation;
said cutting portion including at least one cutting surface extending by about said first radius from said axis of elongation at the juncture of said cutting portion with said main portion, said cutting portion further including at least one other surface extending by said first radius from said axis of elongation; and
said distal end of said body of said tool including a generally circular cross-section, and being tapered from the radius of said cutting portion at the juncture of said cutting portion with said distal end to a lesser radius at more distal locations;
while holding said handle portion of said tool, inserting said distal end of said tool into said corpus to the desired depth, approximately parallel with the axis of elongation of said penis;
if a fibrous region is encountered during said inserting step, adjusting the depth of penetration of said tool into said corpus so that said cutting portion of said tool is adjacent to said fibrous region, and rotating said tool to thereby tend to remove a portion of said fibrous region;
removing said tool from said corpus, whereby a cavity is left therein; and
inserting into said cavity at least a portion of said chamber.

20. A method according to claim 19, wherein said step of obtaining a tool includes the step of obtaining a tool having said first radius approximately equal to a corresponding radius of said chamber.

21. A method according to claim 19, wherein said step of obtaining a tool includes the step of obtaining a plurality of tools, each having a different value of said first radius, and performing said steps of
(a) inserting said distal end of said tool into said corpus, (b) if a fibrous region is are encountered during said inserting step, adjusting the depth of penetration of said tool into said corpus so that said cutting portion of said tool is adjacent to said fibrous region, and rotating said tool to thereby tend to remove a portion of said fibrous region, and (c) removing said tool from said corpus
are performed for each of said plurality of tools, beginning with that one of said tools having the smallest value of said first radius, and proceeding in turn with said tools having the next larger first radius.

22. A method according to claim 19, wherein said step of obtaining a tool includes the step of obtaining a tool in which said cutting surface lies in the surface of a cylinder having a diameter equal to said first radius and coaxial with said axis of elongation.

23. A method according to claim 19, wherein said step of obtaining a tool includes the step of obtaining a tool in which said cutting surface lies in the surface of a cone having a larger diameter which is equal to said first radius, and an axis which is coaxial with said axis of elongation.

24. A kit of tools for aiding insertion of an apparatus into the corpus of a penis, said kit of tools comprising:
a plurality of tools, each said tool defining an axis of elongation, and comprising:
an elongated body defining a distal end, a cutting portion more proximal than said distal end, a main portion more proximal than said cutting portion, and a handle portion more proximal than said main portion;
said main portion of said body of said tool being circular, and defining a first radius about said axis of elongation;
said cutting portion having at least one cutting surface extending by about said first radius from said axis of elongation at the juncture of said cutting portion with said main portion, and at least one other surface which, at any cross-section perpendicular to said axis of elongation, has a radius substantially equal to the radius of said cutting surface at said cross-section; and said distal end of said body of said tool having a generally circular cross-section, and being tapered from the radius of said cutting surface at locations near said cutting portion to a lesser radius at more distal locations; each of said tools of said plurality of tools in one of said kits having a value of said first radius which differs from the value of said first radius of others of said tools in said kit.

25. A kit of tools according to claim 24, wherein said first radii of said tools include values in the range of about 3 to 7 millimeters.

26. A kit of tools according to claim 24, which includes tools having first radii of approximately 3, 4, 5, and 6 millimeters.

27. A kit of tools according to claim 24, wherein said cutting portion is tapered, and said cutting surface extends by a second radius, less than said first radius, at the juncture of said cutting portion with said distal end.

28. A kit of surgical tools for forming a cavity in the corpus of a penis, each of said tools of said kit defining an axis of elongation, and each comprising:

an elongated body defining a distal end, a cutting portion more proximal than said distal end, a main portion more proximal than said cutting portion, and a handle portion more proximal than said main portion;

said main portion of said body of said tool being circular, and defining a first radius about said axis of elongation;

said cutting portion including at least one cutting surface extending by about said first radius from said axis of elongation, and at least one other surface extending by said first radius from said axis of elongation; and said distal end of said body of said tool including a generally circular cross-section, and being tapered from the radius of said cutting portion at the juncture of said cutting portion with said distal end to a lesser radius at more distal locations; wherein at least one of said tools of said kit of tools has said cutting portion on a constant radius from said axis of elongation and said other surface at said constant radius from said axis of elongation, whereby said cutting surface and said other surface lie on the surface of a cylinder; and wherein an other one of said tools of said kit of tools has a tapered cutting portion, and said at least one cutting surface extends by about said first radius from said axis of elongation at the juncture of said cutting portion with said main portion, and by a second radius, less than said first radius, from said axis of elongation at the juncture of said cutting portion with said distal end, and wherein said at least one other tapered surface extends by said first radius from said axis of elongation at said juncture of said cutting portion with said main portion, and by said second radius from said axis of elongation at said juncture of said cutting portion with said distal portion.

* * * * *